(12) United States Patent
Lee, Jr. et al.

(10) Patent No.: US 7,520,877 B2
(45) Date of Patent: Apr. 21, 2009

(54) RADIOFREQUENCY ABLATION SYSTEM USING MULTIPLE PRONG PROBES

(75) Inventors: Fred T. Lee, Jr., Madison, WI (US); Thomas C. Winter, III, Middleton, WI (US); Dieter G. Haemmerich, Madison, WI (US); Lisa A. Sampson, Cambria, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 980 days.

(21) Appl. No.: 10/911,927

(22) Filed: Aug. 5, 2004

(65) Prior Publication Data

US 2005/0010209 A1    Jan. 13, 2005

Related U.S. Application Data

(63) Continuation-in-part of application No. 10/167,681, filed on Jun. 10, 2002, which is a continuation-in-part of application No. 09/873,541, filed on Jun. 4, 2001.

(60) Provisional application No. 60/315,383, filed on Aug. 28, 2001, provisional application No. 60/210,103, filed on Jun. 7, 2000.

(51) Int. Cl.
    *A61B 18/18* (2006.01)
(52) U.S. Cl. .............................. 606/42; 606/47; 606/48; 606/50
(58) Field of Classification Search .................. 606/35, 606/41–48
    See application file for complete search history.

(56) References Cited

U.S. PATENT DOCUMENTS 5,196,008 A * 3/1993 Kuenecke et al. .............. 606/35
5,968,041 A * 10/1999 Edwards ....................... 606/41
6,080,150 A * 6/2000 Gough .......................... 606/41

\* cited by examiner

*Primary Examiner*—David Shay
(74) *Attorney, Agent, or Firm*—Boyle Fredrickson, S.C.

(57) ABSTRACT

Efficient ablation with multiple prong electrodes is obtained by electrically isolating the prongs from each other and rapidly switching electric power between the prongs, between a prong and a ground pad, or both. In this way, power distribution to a tumor can be controlled efficiently without the need to change probe geometry.

17 Claims, 8 Drawing Sheets

RADIOFREQUENCY ABLATION SYSTEM USING MULTIPLE PRONG PROBES

CROSS-REFERENCE TO RELATED APPLICATIONS

This application is in continuation in part of U.S. patent application Ser. No. 10/167,681 filed Jun. 10, 2002, claiming priority to provisional application Ser. No. 60/315,383 filed Aug. 28, 2001 and which is further a continuation-in-part of U.S. application Ser. No. 09/873,541 filed Jun. 4, 2001 claiming the benefit of provisional application Ser. No. 60/210,103 filed Jun. 7, 2000 entitled "Multipolar Electrode System for Radiofrequency Ablation".

STATEMENT REGARDING FEDERALLY SPONSORED RESEARCH OR DEVELOPMENT

This application was made with United States government support awarded the following agencies: NIH HL56143 and NIH DK58839. The United States has certain rights in this invention.

BACKGROUND OF THE INVENTION

The present invention relates to radiofrequency ablation of tumors and the like and, in particular, to a multi-pronged probe device allowing for both bipolar and monopolar ablation from the prongs of the probe.

Ablation of tumors, such as liver (hepatic) tumors, uses heat or cold to kill tumor cells. In cryosurgical ablation, a probe is inserted during an open laparotomy and the tumor is frozen. In radiofrequency ablation (RFA), an electrode is inserted into the tumor and current passing from the electrode into the patient (to an electrical return typically being a large area plate on the patient's skin) destroys the tumor cells through resistive heating. While both methods are generally successful in treating tumor cells, RFA is advantageous in comparison to cryosurgical ablation because the treatment can be delivered percutaneously, without an incision, and thus with less trauma to the patient. In some cases, RFA is the only treatment the patient can withstand. Further, RFA can be completed while the patient is undergoing a CAT scan.

Typically, RFA is provided between an electrode probe and a contact plate provided on the skin of the patient in a process known as monopolar ablation. A simple RFA electrode for use in monopolar ablation is a conductive needle having an uninsulated tip placed within the tumor. The needle is energized with respect to a large area contact plate on the patient's skin by an oscillating electrical signal of approximately 460 kHz. Current flows radially from the tip of the needle and produces a spherical or ellipsoidal zone of heating (depending on the length of the exposed needle tip) and ultimately a lesion within a portion of the zone having sufficient temperature to kill the tumor cells. Treatment is therefore provided in a relatively confined area. For large tumors, therefore, multiple applications of monopolar ablation procedures are often required.

Another type of RFA electrode probe useful in monopolar ablation is an umbrella probe. The umbrella probe uses an umbrella-style electrode in which three or more electrode wires or prongs extend radially from the tip of the electrode shaft after it has been positioned in the tumor, thereby providing an increased electrode area as compared to the needle described above. The prongs are electrically connected and, in operation therefore, all of the prongs operate at the same voltage. As described above with respect to the needle probe, umbrella electrodes are typically energized with respect to a large area contact plate on the patient's skin. Current flowing radially from the tip of each of the prongs of the umbrella probe again produces a spherical or ellipsoidal zone of heating (depending on the length of the exposed needle tip). The combined zones of the prongs of the umbrella probe produces an enlarged zone of heating as compared to the needle probe. Again, however, the deposition of power is in a defined area based on the geometry of the probe, and it is often necessary to reposition the probe and provide multiple applications during treatment.

To further increase the effectiveness of treatment, two umbrellas placed locally around a tumor can also be used in an ablation process known as bipolar ablation. In bipolar ablation, current flows between the two umbrella probe electrodes, which are positioned under the patient's skin, rather than between an electrode and a contact plate. This current flow provides a deposition pattern which "focuses" the energy specifically on the tumor volume between the electrodes producing a lesion with higher heating and more current density between electrodes than would be obtained by a comparable number of monopolar umbrella electrodes operating individually. Bipolar operation therefore can provide more effective treatment of targeted tumors due to greater tissue heating with a single placement of electrodes, improving the speed and effectiveness of the procedure and making it easier to determine the treated volume over procedures where an individual electrode is moved multiple times. However, because two probes are required, bipolar ablation is largely limited to the treatment of only large tumors.

While a number of methods of both monopolar ablation and bipolar ablation are therefore known, each of these methods provides power dispersion to a tumor in a specific pattern based on the geometry of the probe or probes used in the ablation process. These processes, therefore, are fairly limited in that the output of the probes cannot be tailored specifically to a specific tumor. Prior art methods, therefore, provide limited ability to control the deposition of power within the tumor, or to provide the types of ablation most desirable for a given treatment situation without changing the geometry of the probe. Because of these limitations, RFA often fails to kill all of the tumor cells and, as a result, tumor recurrence rates of as high as 50% have been reported.

BRIEF SUMMARY OF THE INVENTION

The present inventors have developed a technique that provides the benefits of bipolar ablation within a multi-prong probe to promote large and uniform lesion sizes. The probe can further combine the benefits of bipolar and either single or multiple, monopolar ablation to provide individual control of the heating in the vicinity of each prong in a multi-prong probe. The technique uses electrically isolated prongs within a multi-prong probe, which can be selectively operated in bipolar or monopolar mode and which, further, can be combined with a circuit switching rapidly between individual prongs. By controlling each prong individually, power deposition around the probe can be controlled without the need to change probe geometries.

Specifically, in one aspect, the present invention provides a radiofrequency ablation system which includes an electrode probe comprising a plurality of prongs, a radiofrequency power source, and at least one ground pad. Each of the plurality of prongs are electrically isolated from the others of the plurality of prongs, such that a switch system communicating with the prongs and the radiofrequency power source selectively connects at least one prong of the probe to the power source to provide for ablative current flow between the connected prong and the ground pad.

In another aspect of the invention, the radiofrequency ablation system comprises a plurality of ground pads, such that the switch system communicates further with the ground pads and a ground connection to selectively connect at least one of the ground pads to the ground connection to provide for ablative current between the connected prong and the connected ground pad.

In yet another aspect of the invention, the radiofrequency ablation system includes a switching system which further communicates with a ground connection such that the switching system can selectively connect one or multiple of the prongs to the power source and another one or multiple of the prongs to the ground connection to provide bipolar ablation. The switch system communicating with the prongs and the radiofrequency power source can also sequentially connects one prong and one ground pad to the power source at a time to provide for monopolar ablative current flow from the selected prong while inhibiting current flow from the other prongs.

In still another aspect of the invention, the probe can be an umbrella shaped, or otherwise shaped (umbrella refers to a specific umbrella shaped electrode; newer models have different shapes) electrode having at least two prongs, or a cluster probe comprised of an array of several parallel prongs.

In still yet another aspect of the invention, the electronic switch controls the relative duration of the connection of the prongs to the power supply according to a control parameter selected from the group consisting of impedance between the connected prong and the ground plane, temperature of the connected prong, a predetermined time setting, and power dissipated between the connected prong and the ground plane. The electronic switch can include, for example, a proportional/integral controller, controlling the switching according to any of the above-referenced parameters.

In another aspect of the invention, a radiofrequency ablation system is provided to include a probe comprising a plurality of electrically isolated prongs, a radiofrequency power source, and a plurality of ground pads. A switch system communicates with the prongs, the ground pads, and the radiofrequency power source to selectively connect at least one prong and at least one of another prong and a ground pad to selectively provide either bipolar or monopolar ablation from the prongs of the probe.

In yet another aspect of the invention, a radiofrequency ablation system is provided. The radiofrequency ablation system includes a probe having a plurality of electrically isolated prongs, a radiofrequency power source, and a switch system communicating with the prongs and the radiofrequency power source to selectively connect a pair of prongs of the probe to the power source to provide for bipolar ablative current flow between the connected prongs.

In yet another aspect of the invention, a method of radiofrequency ablation is provided. The method comprises the steps of placing an electrode including a plurality of electrically isolated prongs in contact with a patient; and selectively connecting pairs of prongs of the electrode to a radiofrequency power source to provide for ablative current flow between the connected pair of prongs while inhibiting current flow between an unconnected pair. The method can further comprise the step of placing at least one ground pad in contact with the patient and selectively connecting the power source between one of the electrically isolated prongs and the ground pad, thereby providing for both bipolar and monopolar ablation from the prongs.

In another aspect of the invention, the relative duration of the connection of the prongs of electrodes to the power supply is according to a control parameter selected from the group consisting of impedance between the connected prong and the ground connection, temperature of at least one of the connected pairs of electrodes, and power dissipated between the connected pairs of the electrodes. The connection of the power supply to one of at least of one of the prongs can be controlled by a proportional/integral controller.

The foregoing and other objects and advantages of the invention will appear from the following description. In this description, reference is made to the accompanying drawings, which form a part hereof, and in which there is shown by way of illustration, a preferred embodiment of the invention. Such embodiment and its particular objects and advantages do not define the scope of the invention, however, and reference must be made therefore to the claims for interpreting the scope of the invention.

DETAILED DESCRIPTION OF THE PREFERRED EMBODIMENT

I. Bipolar Electrode Operation

Figure 1:
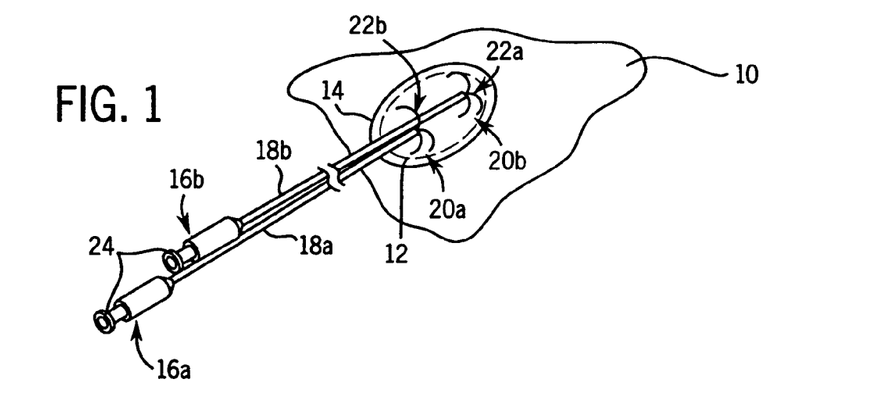
FIG. 1 is a perspective view of two umbrella electrode assemblies providing first and second electrode wires deployed per an allied embodiment of the present invention at opposite edges of a tumor to create a lesion encompassing the tumor by a passing current between the electrodes.

Referring now to FIG. 1, a liver 10 may include a tumor 12 about which a lesion 14 will be created by the present invention using two umbrella-type electrode assemblies 16a and 16b having a slight modification as will be disclosed below. Each electrode assembly 16a and 16b has a thin tubular metallic shaft 18a and 18b sized to be inserted percutaneously into the liver 10. The shafts 18a and 18b terminate, respectively, at shaft tips 20a and 20b from which project trifurcated electrodes 22a and 22b are formed of wires 32. The wires 32 are extended by means of a plunger 24 remaining outside the body once the shafts 18a and 18b are properly located within the liver 10 and when extended, project by an extension radius separated by substantially equal angles around the shaft tips 20a and 20b. The exposed ends of the wires 32 are preformed into arcuate form so that when they are extended from the shafts 18a and 18b they naturally splay outward in a radial fashion. Although the shafts 18a and 18b are shown axially parallel, this is not required and other orientations may be used.

Umbrella electrode assemblies 16a and 16b of this type are well known in the art, but may be modified in one embodiment of the invention, by providing electrical insulation to all outer surfaces of the shafts 18a and 18b and by insulating the tips of the exposed portions of the wires 32. This is in contrast to prior art, umbrella electrode assemblies, which leave the shaft tips 20a and 20b uninsulated and which do not insulate the wires 32. The purpose and effect of these modifications will be described further below.

Per the present invention, the first electrode 22a is positioned at one edge of the tumor 12 and the other electrode 22b positioned opposite the first electrode 22a across the tumor 12 center. The term "edge" as used herein refers generally to locations near the periphery of the tumor 12 and is not intended to be limited to positions either in or out of the tumor 12, whose boundaries in practice may be irregular and not well known. Of significance to the invention is that a part of the tumor 12 is contained between the electrodes 22a and 22b.

Figure 2:
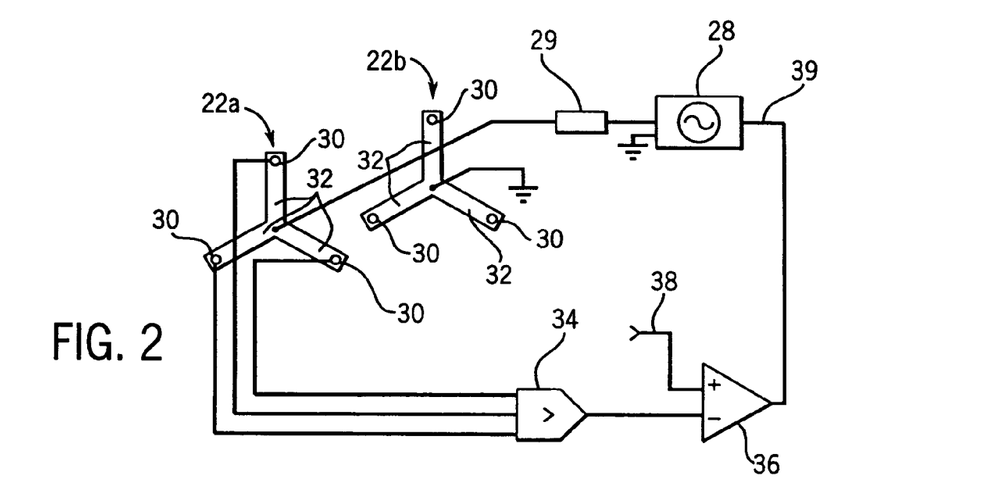
FIG. 2 is a schematic representation of the electrodes of FIG. 1 as connected to a voltage-controlled oscillator and showing temperature sensors on the electrode wires for feedback control of oscillator voltage.

Referring now to FIGS. 1 and 2, electrode 22a may be attached to a voltage-controlled power oscillator 28 of a type well known in the art providing a settable frequency of alternating current power whose voltage amplitude (or current or power output) is controlled by an external signal. The return of the power oscillator 28 is connected to electrodes 22b also designated as a ground reference. When energized, the power oscillator 28 induces a voltage between electrodes 22a and 22b causing current flow therebetween.

Figure 4:
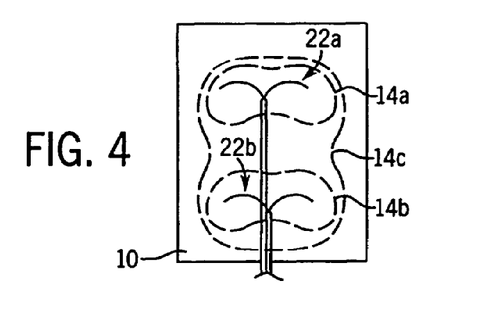
FIG. 4 is a simplified elevational cross-section of a tumor showing the first and second electrode positions and comparing the lesion volume obtained from two electrodes operating per the present invention, compared to the lesion volume obtained from two electrodes operating in a monopolar fashion.

Referring now to FIG. 4, prior art operation of each electrode 22a and 22b being referenced to a skin contract plate (not shown) would be expected to produce lesions 14a and 14b, respectively, per the prior art. By connecting the electrodes as shown in FIG. 2, however, with current flow therebetween, a substantially larger lesion 14c is created. Lesion 14c also has improved symmetry along the axis of separation of the electrodes 22a and 22b. Generally, it has been found preferable that the electrodes 22a and 22b are separated by 2.5 to 3 cm for typical umbrella electrodes or by less than four times their extension radius.

Referring again to FIG. 2, temperature sensors 30, such as thermocouples, resistive or solid-state-type detectors, may be positioned at the distal ends of each of the exposed wires 32 of the tripartite electrodes 22a and 22b. For this purpose, the wires 32 may be small tubes holding small conductors and the temperature sensors 30 as described above. Commercially available umbrella-type electrode assemblies 16a and 16b currently include such sensors and wires connecting each sensor to a connector (not shown) in the plunger 24.

In a first embodiment, the temperature sensors 30 in electrode 22a are connected to a maximum determining circuit 34 selecting for output that signal, of the three temperature sensors 30 of electrode 22 that has the maximum value. The maximum determining circuit 34 may be discrete circuitry, such as may provide precision rectifiers joined to pass only the largest signal, or may be implemented in software by first converting the signals from the temperature sensors 30 to digital values, and determining the maximum by means of an executed program on a microcontroller or the like.

The maximum value of temperature from the temperature sensors 30 is passed by a comparator 36 (which also may be implemented in discrete circuitry or in software), which compares the maximum temperature to a predetermined desired temperature signal 38 such as may come from a potentiometer or the like. The desired temperature signal is typically set just below the point at which tissue boiling, vaporization, or charring will occur.

The output from the comparator 36 may be amplified and filtered according to well known control techniques to provide an amplitude input 39 to the power oscillator 28. Thus, it will be understood that the current between 22a and 22b will be limited to a point where the temperature at any one of temperature sensors 30 approaches the predetermined desired temperature signal 38.

While the power oscillator 28 as described provides voltage amplitude control, it will be understood that current amplitude control may instead also be used. Accordingly, henceforth the terms voltage and current control as used herein should be considered interchangeable, being related by the impedance of the tissue between the electrodes 22b and 22a.

In an alternative embodiment, current flowing between the electrodes 22a and 22b, measured as it flows from the power oscillator 28 through a current sensor 29, may be used as part of the feedback loop to limit current from the power oscillator 28 with or without the temperature control described above.

In yet a further embodiment, not shown, the temperature sensors 30 of electrode 22b may also be provided to the maximum determining circuit 34 for more complete temperature monitoring. Other control methodologies may also be adopted including those provided for weighted averages of temperature readings or those anticipating temperature readings based on their trends according to techniques known to those of ordinary skill in the art.

Figure 3:
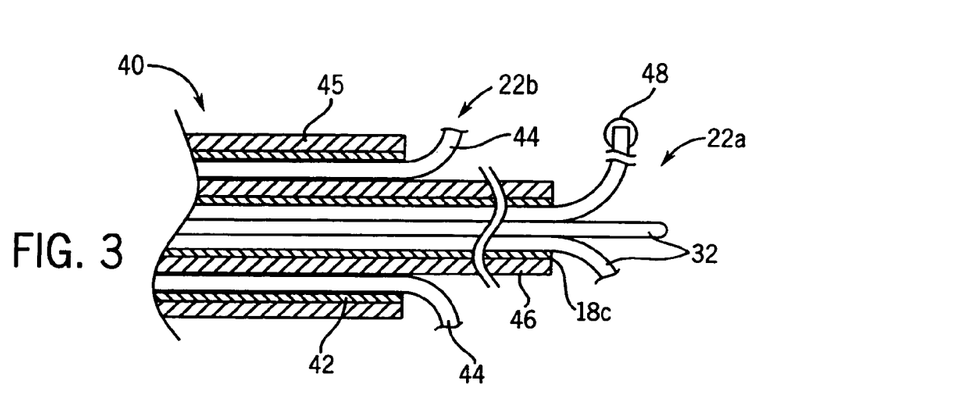
FIG. 3 is a fragmentary cross-sectional view of a tip of a combined electrode assembly providing for the first and second electrode wires of FIG. 1 extending from a unitary shaft arranging the wires of the first and second electrodes in concentric tubes and showing an insulation of the entire outer surface of the tubes and of the tips of the electrode wires.

Referring now to FIG. 3, the difficulty of positioning two separate electrode assemblies 16a and 16b per FIG. 1 may be reduced through the use of a unitary electrode 40 having a center tubular shaft 18c holding within its lumen, the wires 32 of first electrode 22a and a second concentric tubular shaft 42 positioned about shaft 18c and holding between its walls and shaft 18c wires 44 of the second electrode 22b. Wires 44 may be tempered and formed into a shape similar to that of wires 32 described above. Shafts 18c and 42 are typically metallic and thus are coated with insulating coatings 45 and 46, respectively, to ensure that any current flow is between the exposed wires 32 rather than the shafts 18c and 42.

As mentioned above, this insulating coating 46 is also applied to the tips of the shafts 18a and 18b of the electrode assemblies 16a and 16b of FIG. 1 to likewise ensure that current does not concentrate in a short circuit between the shafts 18a and 18b but, in fact, flows from the wires 32 of the wires of electrodes 22a and 22b.

Other similar shaft configurations for a unitary electrode 40 may be obtained including those having side-by-side shafts 18a and 18b attached by welding or the like.

Kits of unitary electrode 40 each having different separations between first electrode 22a and second electrode 22a may be offered suitable for different tumor sizes and different tissue types.

As mentioned briefly above, in either of the embodiments of FIGS. 1 and 3, the wires 32 may include insulating coating 46 on their distal ends removed from shafts 18c and 42 to reduce high current densities associated with the ends of the wires 32.

In a preferred embodiment, the wires of the first and second electrodes 22a and 22b are angularly staggered (unlike as shown in FIG. 2) so that an axial view of the electrode assembly reveals equally spaced non-overlapping wires 32. Such a configuration is also desired in the embodiment of FIG. 2, although harder to maintain with two electrode assemblies 16a and 16b.

Figure 6:
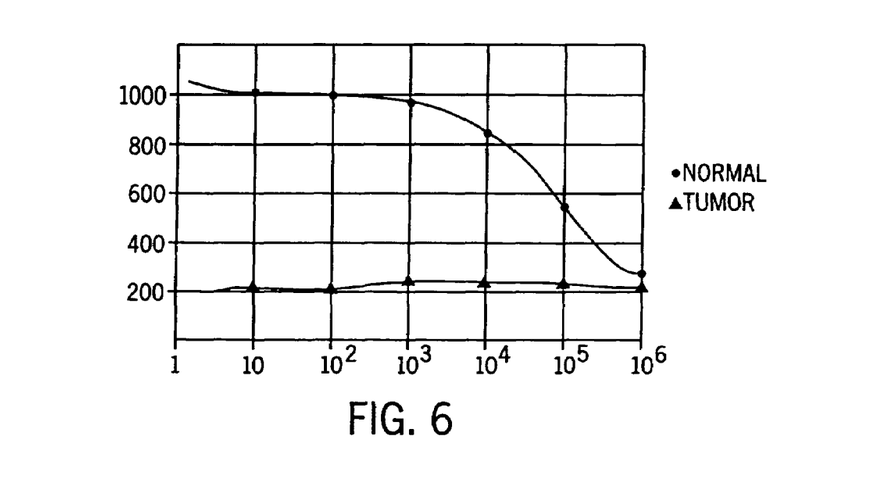
FIG. 6 is a graph plotting resistivity in ohm-centimeters vs. frequency in hertz for tumorous and normal liver tissue, showing their separation in resistivity for frequencies below approximately 100 kHz.

The frequency of the power oscillator 28 may be preferentially set to a value much below the 450 kHz value used in the prior art. Referring to FIG. 6, at less than 100 kHz and being most pronounced and frequencies below 10 kHz, the impedance of normal tissue increases to significantly greater than the impedance of tumor tissue. This difference in impedance is believed to be the result of differences in interstitial material between tumor and regular cell tissues although the present inventors do not wish to be bound by a particular theory. In any case, it is currently believed that the lower impedance of the tumorous tissue may be exploited to preferentially deposit energy in that tissue by setting the frequency of the power oscillator 28 at values near 10 kHz. Nevertheless, this frequency setting is not required in all embodiments of the present invention.

Importantly, although such frequencies may excite nerve tissue, such as the heart, such excitation is limited by the present bipolar design.

Figure 5:
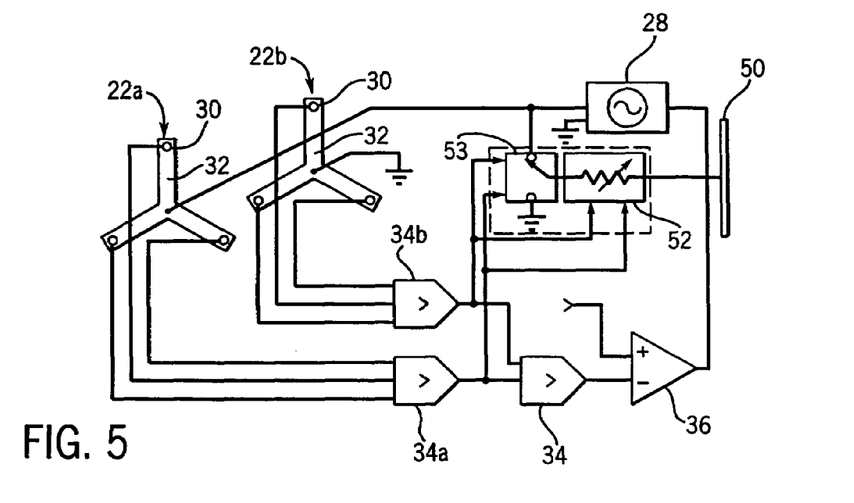
FIG. 5 is a figure similar to that of FIG. 2 showing electrical connection of the electrodes of FIG. 1 or FIG. 3 to effect a more complex control strategy employing temperature sensing from each of the first and second electrodes and showing the use of a third skin contact plate held in voltage between the two electrodes so as to provide independent current control for each of the two electrodes.

Referring now to FIG. 5, the local environment of the electrodes 22a and 22b may differ by the presence of a blood vessel or the like in the vicinity of one electrode such as substantially reduces the heating of the lesion 14 in that area. Accordingly, it may be desired to increase the current density around one electrode 22a and 22b without changing the current density around the other electrode 22a and 22b. This may be accomplished by use of a skin contact plate 50 of a type used in the prior art yet employed in a different manner in the present invention. As used herein, the term contact plate 50 may refer generally to any large area conductor intended but not necessarily limited to contact over a broad area at the patient's skin.

In the embodiment of FIG. 5, the contact plate 50 may be referenced through a variable resistance 52 to either the output of power oscillator 28 or ground per switch 53 depending on the temperature of the electrodes 22a and 22b. Generally, switch 53 will connect the free end of variable resistance 52 to the output of the power oscillator 28 when the temperature sensors 30 indicate a higher temperature on electrode 22b than electrode 22a. Conversely, switch 53 will connect the free end of variable resistance 52 to ground when the temperature sensors 30 indicate a lower temperature on electrode 22b than electrode 22a. The comparison of the temperatures of the electrodes 22a and 22b may be done via maximum determining circuits 34a and 34b, similar to that described above with respect to FIG. 2. The switch 53 may be a comparator-driven, solid-state switch of a type well known in the art.

The output of the maximum-determining circuits 34a and 34b each connected respectively to the temperature sensors 30 of electrodes 22a and 22b may also be used to control the setting of the variable resistance 52. When the switch 53 connects the resistance 52 to the output of the power oscillator 28, the maximum-determining circuits 34a and 34b serve to reduce the resistance of resistance 52 as electrode 22b gets relatively hotter. Conversely, when the switch 53 connects the resistance 52 to ground, the maximum-determining circuits 34a and 34b serve to reduce the resistance of resistance 52 as electrode 22a gets relatively hotter. The action of the switch 53 and variable resistance 52 is thus generally to try to equalize the temperature of the electrodes 22a and 22b.

If electrode 22a is close to a heat sink such as a blood vessel when electrode 22b is not, the temperature sensors 30 of electrode 22a will register a smaller value and thus, the output of maximum-determining circuit 34a will be lower than the output of maximum-determining circuit 34b.

The resistance 52 may be implemented as a solid-state device according to techniques known in the art where the relative values of the outputs of maximum-determining circuits 34a and 34b control the bias and hence resistance of a solid-state device or a duty-cycle modulation of a switching element or a current controlled voltage source providing the equalization described above.

Figure 7:
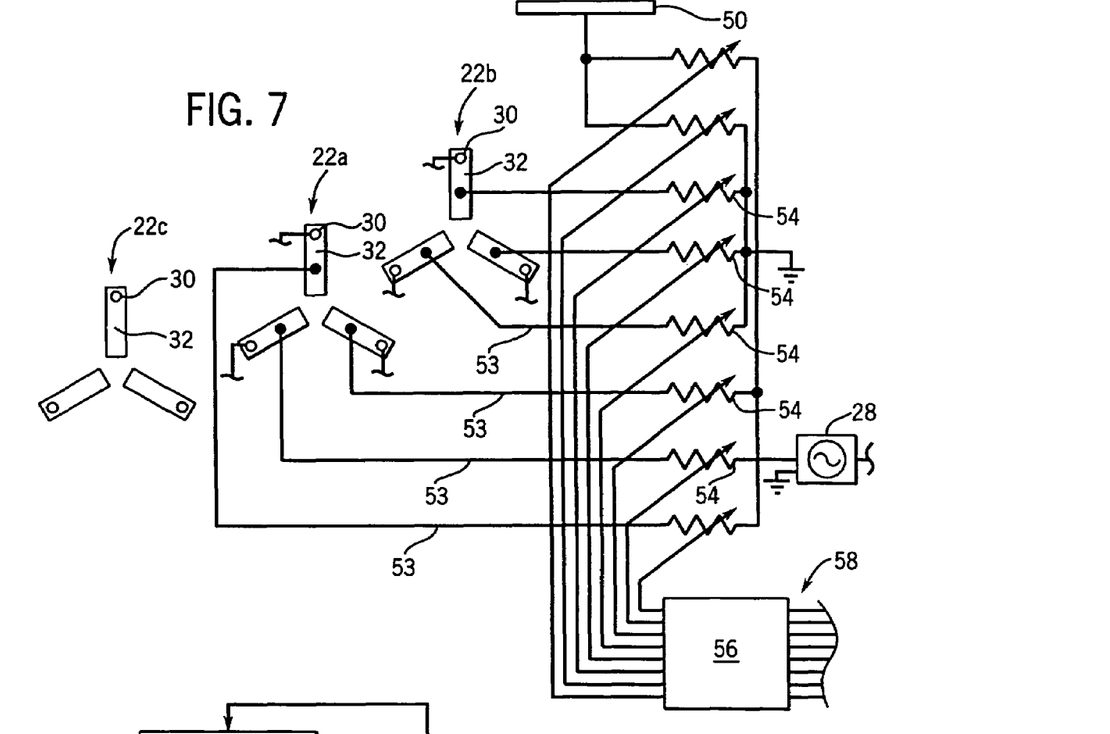
FIG. 7 is a figure similar to that of FIGS. 2 and 5 showing yet another embodiment in which wires of each of the first and second electrodes are electrically isolated so that independent voltages or currents or phases of either can be applied to each wire to precisely tailor the current flow between that wire and the other electrodes.

Referring now to FIG. 7, these principles may be applied to a system in which each wire 32 of electrodes 22a and 22b is electrically isolated within the electrode assemblies 16a and 16b and driven by separate feeds by switch 53 through variable resistances 54 connected either to the power oscillator 28 or its return. Electrically isolated means, in this context, that there is not a conductive path between the electrodes 22a and 22b except through tissue prior to connection to the power supply or control electronics. As noted before, a phase difference can also be employed between separate feeds from switch 53 to further control the path of current flow between electrode wires 32. This phase difference could be created, e.g. by complex resistances that create a phase shift or by specialized waveform generators operating according to a computer program, to produce an arbitrary switching pattern. The values of the resistances 54 are changed as will be described by a program operating on a controller 56. For this purpose, the variable resistances 54 may be implemented using solid-state devices such as MOSFETs according to techniques known in the art.

Likewise, similar variable resistances 54 also controlled by a controller 56 may drive the contact plate 50.

For the purpose of control, the controller 56 may receive the inputs from the temperature sensors 30 (described above) of each wire 32 as lines 58. This separate control of the voltages on the wires 32 allows additional control of current flows throughout the tumor 12 to be responsive to heat sinking blood vessels or the like near any one wire.

Figure 8:
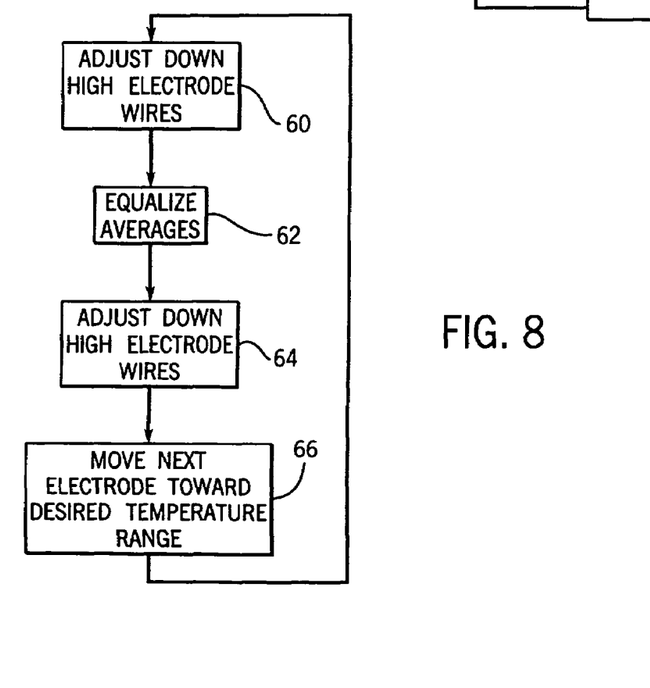
FIG. 8 is a flow chart of a program as may be executed by the controller of FIG. 7 in utilizing its multi-electrode control.

Referring to FIG. 8, one possible control algorithm scans the temperature sensors 30 as shown by process block 60. For each temperature sensor 30, if the temperature at that wire 32 is above a "ceiling value" below a tissue charring point, then the voltage at that wire is reduced. This "hammering down" process is repeated until all temperatures of all wires are below the ceiling value.

Next at process block 62, the average temperature of the wires on each electrode 22a and 22b is determined and the voltage of the contact plate 50 is adjusted to incrementally equalize these average values. The voltage of the contact plate 50 is moved toward the voltage of the electrode 22 having the higher average.

Next at process block 64, the hammering down process of process block 60 is repeated to ensure that no wire has risen above its ceiling value.

Next at process block 66 one wire in sequence at each occurrence of process block 66 is examined and if its temperature is below a "floor value" below the ceiling value, but sufficiently high to provide the desired power to the tumor, the voltage at that wire 32 is moved incrementally away from the voltage of the wires of the other electrode 22. Conversely, if the wire 32 is above the floor value, no action is taken.

Incrementally, each wire 32 will have its temperature adjusted to be within the floor and ceiling range by separate voltage control. It will be understood that this process can be applied not only to the control parameter of temperature but also to other desired control parameters including, for example, impedance.

As shown in FIG. 7, this process may be extended to an arbitrary number of electrodes 22 including a third electrode set 22c whose connections are not shown for clarity.

While this present invention has been described with respect to umbrella probes, it will be understood that most of its principles can be exploited using standard needle probes. Further, it will be understood that the present invention is not limited to two electrode sets, but may be used with multiple electrode sets where current flow is predominantly between sets of the electrodes. The number of wires of the umbrella electrodes is likewise not limited to three and commercially available probes suitable for use with the present invention include a 10 wire version. Further, although the maximum temperatures of the electrodes were used for control in the above-described examples, it will be understood that the invention is equally amenable to control strategies that use minimum or average temperature or that measure impedance or use predetermined switching times.

II. Multiplexed Monopolar Electrode Operation

Figure 9:
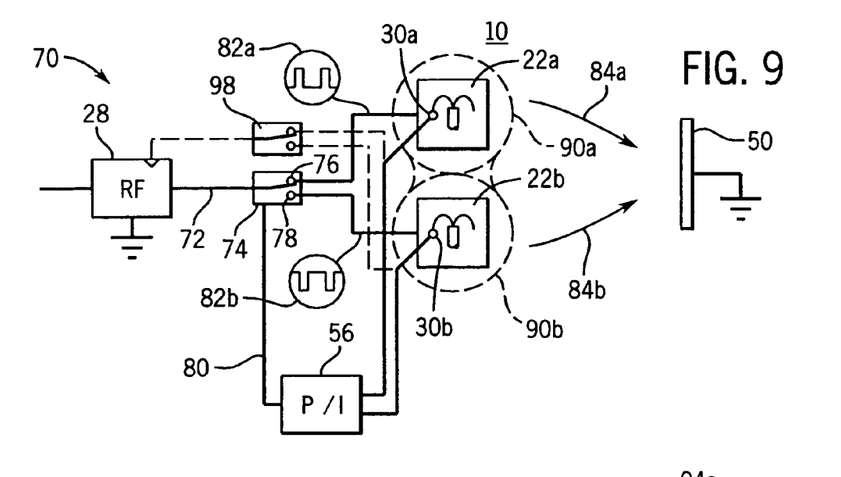
FIG. 9 is a schematic block diagram of a second embodiment of the invention providing for multiplexed monopolar operation of multiple electrodes and showing a controller connecting a radiofrequency source to multiple, monopolar electrodes through a switch cycling between the electrodes.

Referring now to FIG. 9, a multiplexed monopolar system 70 provides a power oscillator 28 having a power output 72 at which a radiofrequency signal is connected to the pole of a single pole double throw switch 74. Switch 74 is preferably implemented as a solid-state switch according to techniques well known in the art preferably, but not limited to, switching at speeds over 20 kilohertz.

A first throw 76 of the switch 74 is connected to a first electrode 22a being an umbrella-type electrode as described above with the tines of the umbrella electrically joined. At least one tine may include a temperature sensor 30a.

A second throw 78 of the switch 74 is connected to second electrode 22b also having a temperature sensor 30b.

The electrodes 22a and 22b are placed as described above flanking the volume of a tumor or in separate tumors as may be desired. If a single tumor is being treated, the electrodes 22a and 22b will be proximate to each other typically less than three times the diameter of the extension radius of the tines of the electrodes 22a and 22b. Conversely, to the bipolar embodiment, in the multiplexed monopolar electrode operation, there is no limitation on the orientation at which the probes are inserted. It is also understood that the described technique can be extended to any number of electrodes.

In one embodiment, signals from the temperature sensors 30a and 30b are received by a controller 56, which subtracts the temperatures to create a temperature difference signal that is received by a proportional/integral (PI) type controller 56. PI controllers are well known in the art and produce an output signal that is a function of a first control constant $K_1$ times the input difference signal, plus a second control constant $K_2$ times the integral of the input difference signal. The PI controller 56 in this case produces a control signal 80 implemented as an electrical square wave whose further properties will be described below.

As an alternative to the temperature difference signal, the PI controller may accept a variety of other control inputs including impedance, temperature, power, absolute time (for a regular switching among electrodes), or the difference between the impedance, temperature, or power of one or more electrodes and other similar control inputs.

Alternatively to the PI controller, any other conceivable control mechanism can be implemented to distribute the power to two or more probes.

Figure 10:
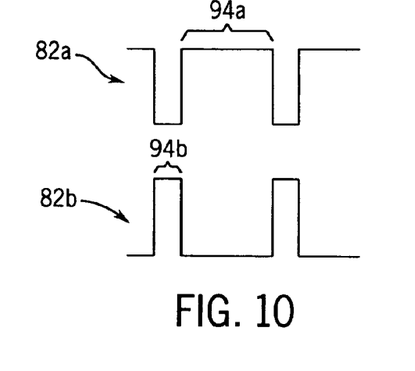
FIG. 10 is a timing diagram of the operation of the switch of FIG. 9 showing complimentary operation of two electrodes and control of the duty-cycle of operation for further electrode control.

Referring also to FIG. 10, generally, the square wave of the control signal 80 controls the operation of the pole of the switch 74 to create a switching pattern 82a for electrode 22a and a switching pattern 82b for electrode 22b. The switching patterns 82a and 82b describe the position of the pole of the switch 74 and thus a modulation envelope of the radiofrequency waveform of the output 72 seen at each electrode 22a and 22b. During times when the pole of the switch 74 is connected to throw 76, the wave form 82a is in a high state indicating that radiofrequency power is being supplied to electrode 22a. Conversely, when the pole of the switch 74 is connected to throw 78, wave form 82b is high indicating that radiofrequency energy is being supplied to electrode 22b.

As is illustrated in the preferred embodiment, signals 82a and 82b are exact complements indicating that only one of electrodes 22a and 22b will be receiving electrical power at any given instant and yet the power from the power oscillator 28 is fully utilized. That is, when electrode 22a is energized, current flows only between electrode 22a and contact plate 50 (as indicated by arrow 84a of FIG. 9). Conversely, when electrode 22b is energized, current flows only between electrode 22b and contact plate 50 (as indicated by 84b of FIG. 9). When only one of electrodes 22a and 22b is activated at a given time, there is no shielding that would tend to distort lesion volume 90a about electrode 22b or 90b about electrode 22b and that would otherwise occur if electrodes 22a and 22b were simultaneously energized. Note, however, that some overlap of the "on" states of electrodes 22a and 22b may be tolerated if it is minor in comparison to the period of non-overlap.

A period of time 94a during which electrode 22a is activated expressed as a ratio with a period of time 94 during which electrode 22b is activated, defines a "duty-cycle". The control signal 80 forming the output of the PI controller 56 controls this duty-cycle so that power is steered preferentially to one of electrodes 22a and 22b having the lower temperature. In this way, the controller 56 may act to bring their relative temperatures of the two electrodes 22a and 22b into equilibrium. Alternatively, the duty-cycle may be controlled based on impedance between the connected pairs of electrodes or power dissipated between the connected pairs of the electrodes. The speed at which the duty-cycle is adjusted in response to temperature differences and controlled by the settings of $K_1$ and $K_2$ described above and is adjusted to reflect average temperatures at the electrodes 22a and 22b whose actual temperatures may deviate instantaneously with the switching of power.

The frequency of the switching of switch 74 is selected to be fast compared to the cooling time of the tissue (e.g., 2 Hz or above). Higher switching speeds above 10 kHz and near 20 kHz may be preferred to avoid low-frequency components that could excite nerves and tissue, especially cardiac tissue. Switching is performed preferentially at the zero-crossings of the signal provided by the radiofrequency power supply to avoid transient currents.

The PI controller may also provide a limiter reducing the average power delivered to electrodes 22a and 22b when a threshold temperature (approximately 95 degrees C.) is reached by decreasing simultaneously periods 94a and 94b while preserving their ratio. In this case, the patterns 82a and 82b are no longer complementary but still have non-overlapping high states.

The power output of the radiofrequency power supply may further be controlled by the temperature or impedance of electrodes 22a and 22b. In this embodiment, patterns 82a and 82b are complementary. The switch is controlled in a way to bring temperatures of electrodes 22a and 22b to equilibrium. The power output of the radiofrequency power supply is adjusted to bring average temperature of electrodes 22a and 22b to a set temperature, typically below the temperature where charring and boiling would occur.

In an alternative embodiment shown in FIG. 9, the temperature sensors 30a and 30b may be routed as indicated by dotted lines 96 to a secondary switch 98 being a single pole, double throw switch whose pole is connected to a temperature input on a standard power oscillator 28. In this case, the power oscillator 28 may be directly controlled so as to reduce its output voltage or current as a function of the temperature received from a given temperature probe 30a or 30b such as will alternate according to the operation of the switch 74. Thus during the time the power oscillator 28 is delivering power to electrode 22a, it will also be receiving the temperature from temperature sensor 30a to control it appropriately. Then when switch 74 changes state and the power oscillator is connected to electrode 22b, the power oscillator may receive a temperature signal from temperature 30b.

Figure 11:
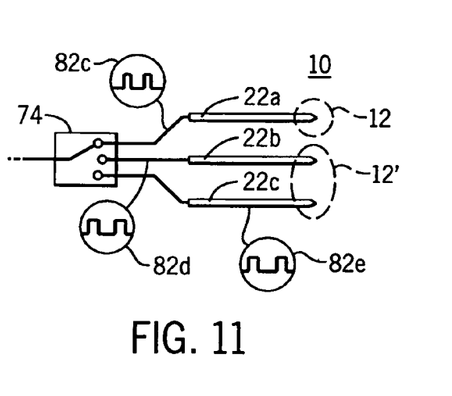
FIG. 11 is a fragmentary view of a further embodiment of the switch of FIG. 9 showing its extension for operation of three electrodes.

Referring now to FIG. 11, the switch 74 may in fact accommodate any number of electrodes 22a, 22b, and 22c here depicted as needle electrodes in multiple tumors 12 and 12'. Thus the present invention may provide the benefits of locating an arbitrary number of electrodes in place about a tumor at one instant and then providing essentially simultaneous treatment of the volume with combined thermal effects without the need to move electrodes.

Figure 12:
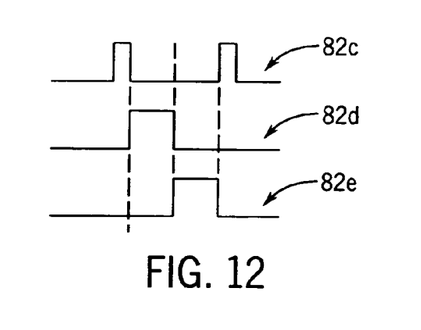
FIG. 12 is a timing diagram of the power received by the electrodes using a switch per the embodiment of FIG. 11.

As depicted, switch 74 is a single pole, triple throw switch with one throw connected to each of electrodes 22a, 22b and 22c to provide modulated radiofrequency energy according to patterns 82c, 82d, and 82e as shown in FIG. 12. Switching patterns 82c, 82d, and 82e are analogous to switching patterns 82a and 82b described above except for the fact that the duty-cycle of three wave forms is independently controlled 82a, 82b and 82c to proportionally move power to the lowest temperature electrode 22, and they are no longer complementary but simply have non-overlapping on times. Ideally, when one or more electrodes 22 have temperatures below the threshold, one of the switching patterns 82c, 82d, and 82e is on at all times. In certain control algorithms there may be cycles, where power is not steered to any of the probes. In that case on pole of the multi throw switch is not connected to any probe, or is connected to some element dissipating the power.

III. Multiplexed Prong Operation

Figure 13:
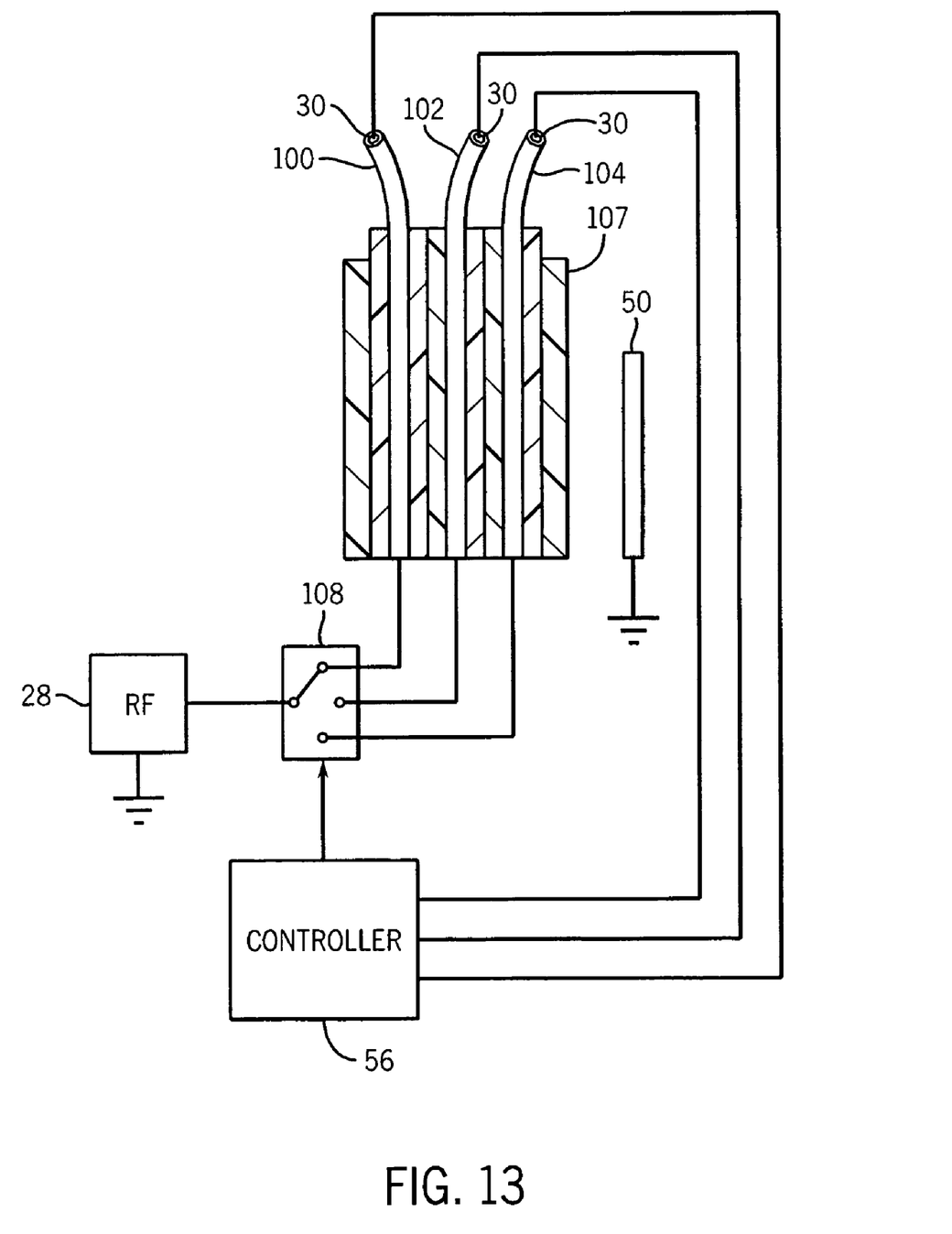
FIG. 13 is a cutaway view of a multi-prong probe including electrically isolated probes and a switching system for providing monopolar ablation from each of the prongs.

Referring now to FIG. 13 an alternate embodiment of an electrode 101 is shown. As described with reference to FIG. 7 above, here the probe or electrode 101 includes a plurality of prongs 100, 102, and 104 each of which are electrically isolated from the other prongs with, for example, electrical insulation 106, and each of which are housed within a single shaft 107, which can also be electrically isolated from the prongs 100, 102, and 104. The prongs 100, 102, and 104 can be curved outward to provide an umbrella configuration, can be arranged in a parallel configuration, or be otherwise configured. The individual prongs 100, 102, and 104 are coupled to a single pole multi-throw switch 108 the pole of which is connected to an RF power supply 28. The number of throws is equivalent to the number of prongs in the electrode 101, and therefore as shown here, is a triple throw switch. A contact plate or ground pad 50 is also provided. In operation, each prong 100, 102, and 104 of the probe 101 can be individually activated to provide monopolar RF ablation, between the active prong and the ground pad 50. A controller 56 coupled to the single pole multi-throw switch 108 can also be provided to control switching between the prongs 100, 102, and 104, as well as activation time and other variables. As described above, a temperature sensor 30 can be positioned on each of the prongs 100, 102, and 104 and temperature feedback provided to the controller 56 which, as described above, can be a PID controller which switches between the prongs 100, 102, and 104 based on the temperature reading received from the sensors 30, or in other parameters, such as impedance, power, absolute time, or the difference between the impedance, temperature, or power of one or more prongs or similar control inputs, as described above. Although one ground pad 50 is shown, it will be apparent that multiple ground pads can be provided, and that the ground pads can be switched into and out of operation with a switch, as described below. Furthermore, the shaft 107 can also be selectively connected to the power source 28. Because each of the prongs 100, 102, and 104 is electrically independent, and individually activated there are no electrical interactions between the prongs and improve treatment of the center of the zone of ablation can be realized, for example.

Figure 14:
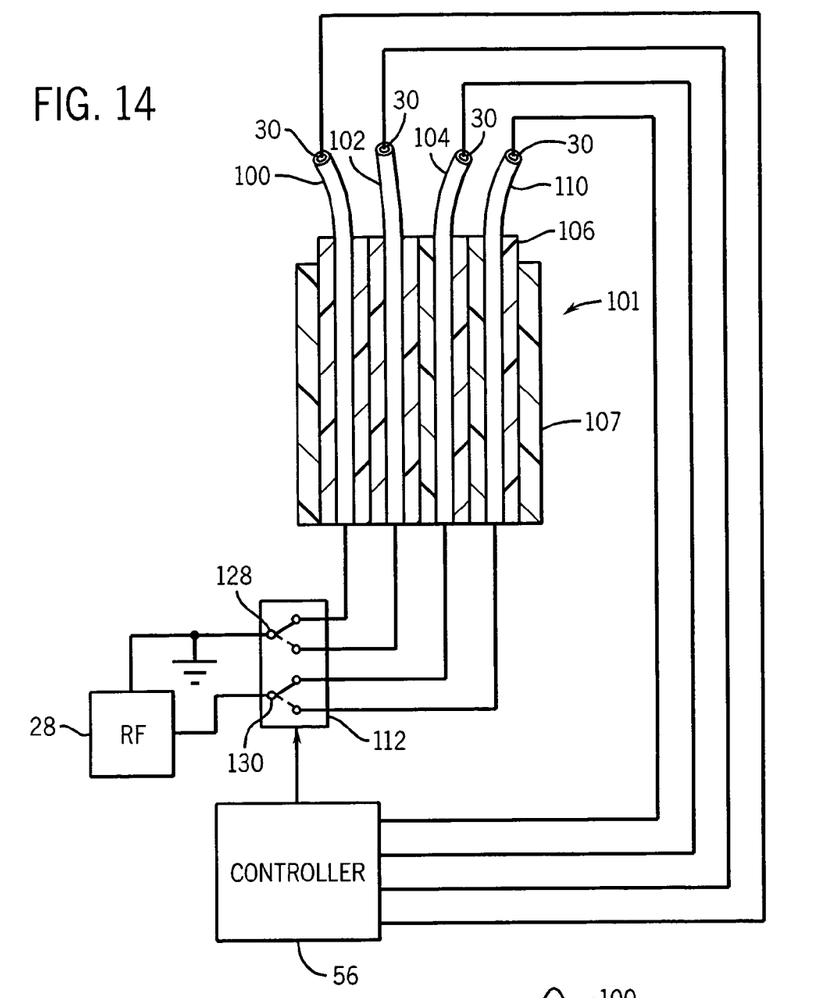
FIG. 14 is a cutaway side view of the multi-prong probe of FIG. 13 connected to a switching system for providing bipolar ablation between the prongs of the probe.

Referring now to FIG. 14 another embodiment of an electrode 101 as described above is shown. Here the probe includes an even number of prongs 100, 102, 104, and 110 each of which is, as described above, isolated or electrically insulated from the adjacent prongs through insulation 106. The prongs 100, 102, 104, and 110 are each coupled to a double pole multi-throw switch where the number of throws are determined as half of the number of prongs in the probe 101, and therefore, in the illustration, is a double pole, double throw switch. One pole of the double pole, double throw switch 128 is coupled to a ground connection 114 while a second pole 130 is coupled to an RF power source 28 also referenced to the ground connection 114.

Figure 15:
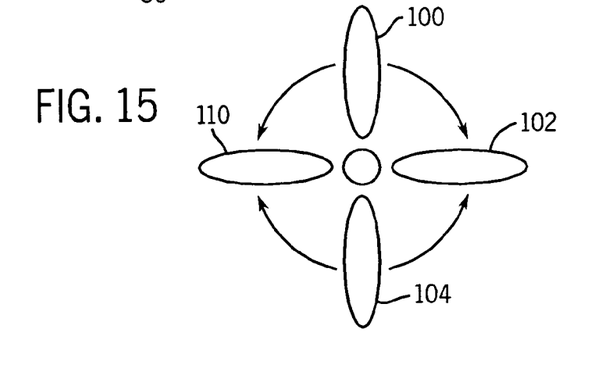
FIG. 15 is a top view of the multi-prong probe of FIG. 14 illustrating current flow to form a center lesion.

Referring now to FIG. 15, in operation opposed pairs of prongs 100 and 104 and 102 and 110, respectively, are activated by the controller 56 to provide bipolar ablation between the respective pairs of prongs. By switching opposed pairs of prongs, a high temperature switched bipolar lesion can be formed in the center of the prongs.

As described above with reference to FIG. 13, each of the prongs 100, 102, 104, and 110 can include a temperature sensor 30 which provides feedback to the controller 56 which can, based on this feedback, determine when to switch between the various pairs of prongs to maintain power and temperature levels at a determined level. Although not shown, it will be apparent that a triple throw switch can also be used to provide an open connection for deactivating the prongs as desired to maintain power and temperature at a selected level.

Although shown for a four-pronged probe, a probe having a 10 prong substantially circular array is preferred, with a switching pattern in which pairs of diametrically opposed prongs are sequentially activated. As described above, switching in this way results in a high temperature switched bipolar lesion in the center of the prongs. Furthermore, although an even number of prongs is shown, a circular array including an odd number of prongs can also be provided, with switching provided between substantially opposed offset prongs.

Figure 16:
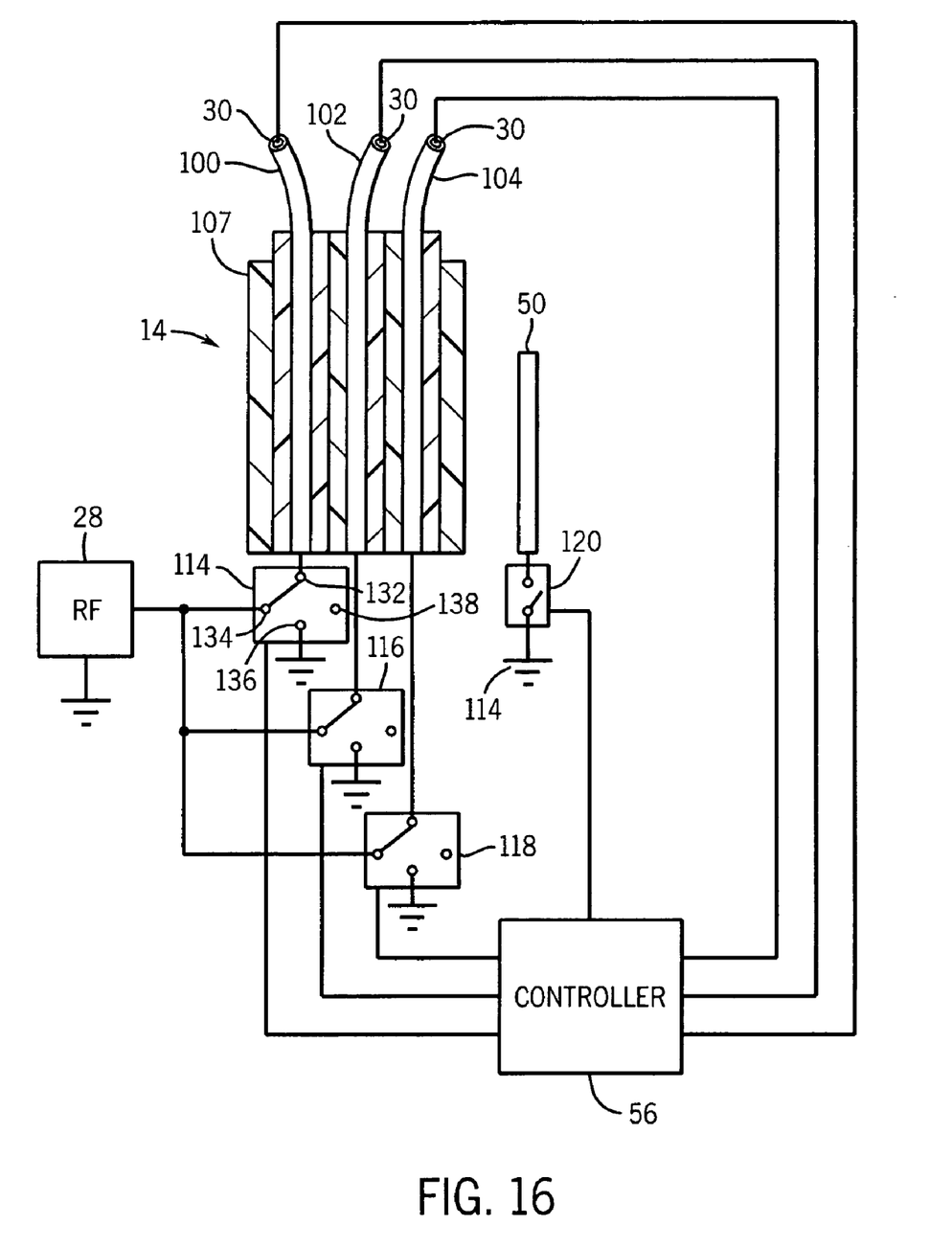
FIG. 16 is a cutaway side view of the multi-prong probe of FIG. 13 connected to a switching system for selectively providing bipolar or monopolar ablation with the probe.

Referring now to FIG. 16 another embodiment of an RF probe 101 is shown. Here, again, each of the prongs 100, 102, and 104 are electrically isolated from the other of the prongs with insulation 106. Each of the prongs 100, 102, and 104 is coupled to a single pole triple throw switch 114, 116, and 118, respectively. Referring specifically to single pole triple throw switch 114 the pole 132 is connected to the prong 100 and the throws 134, 136, and 138 are connected to the RF power supply 28, a ground connection 114, and to an electrically open position respectively. Each of the switches 114, 116, and 118 are further coupled to a controller 56 which, based on feedback from temperature sensors 30 or other types of feedback as described above, determines which of the prongs are connected to the RF power supply 28, which are connected to the ground connection 114, and which are left open. Bipolar ablation can therefore be provided between pairs of the prongs 100, 102, and 104. A ground pad 50 can also be provided and selectively coupled through a single pole, single throw switch 120 to the ground connection 114 enabling monopolar ablation. To provide monopolar ablation from any of the prongs 100, 102, or 104 the controller 56 can activate any of the switches 114, 116, and 118 to tie the prongs 100, 102, or 104 to the RF supply 28, while switch 120 is activated to connect the ground pad 50 to a circuit ground connection 114. Alternatively, each of the prongs 100, 102, and 104 can be tied to the RF power supply 28 simultaneously to provide conventional ablation in which all of the prongs of the probe are simultaneously activated. Conventional, monopolar and bipolar ablation can therefore be combined in order to provide distribution of power appropriate to a given treatment situation. Furthermore, by switching rapidly between the different application patterns, power deposition can be controlled without changing probe geometry.

Figure 17:
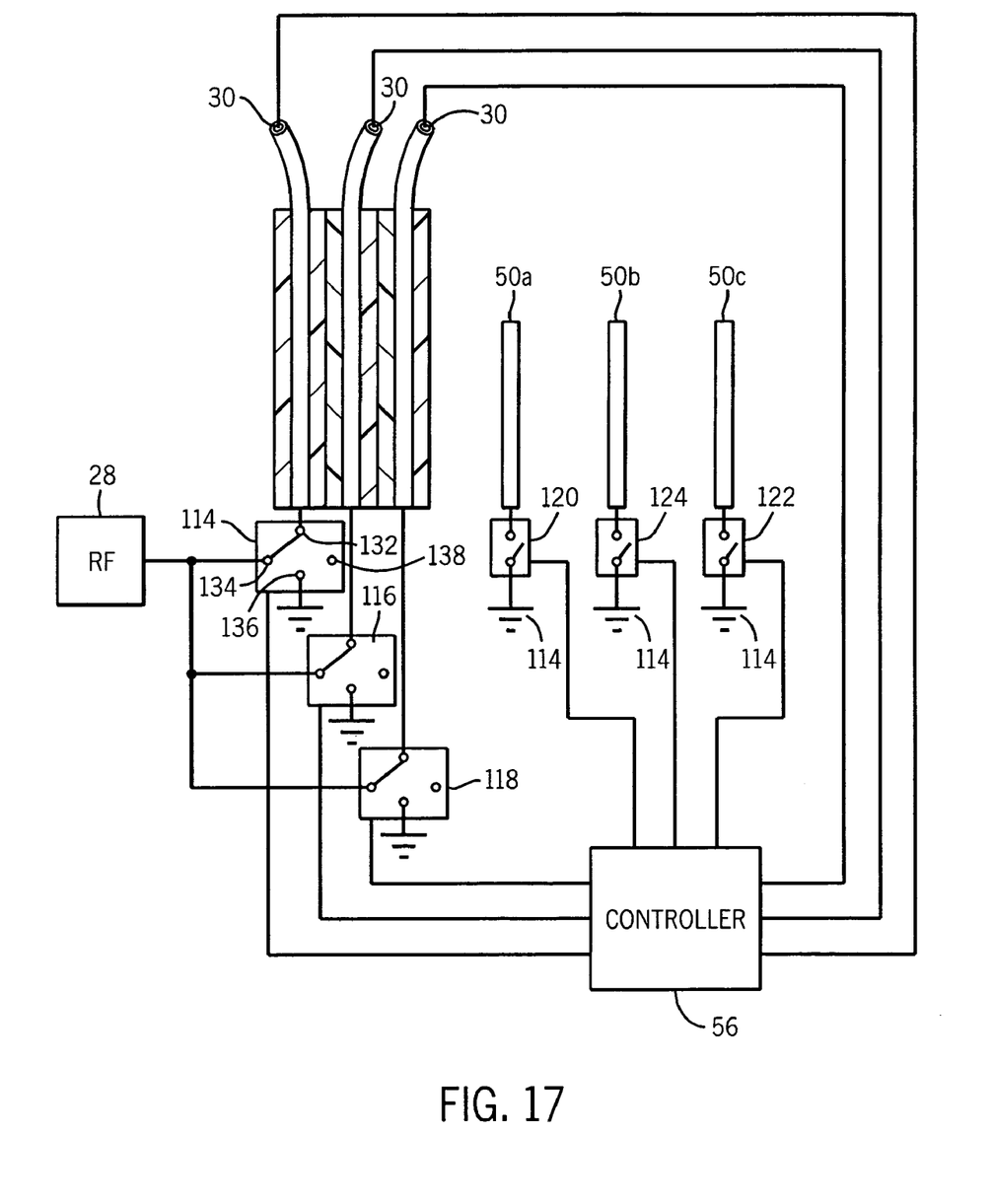
FIG. 17 is a view of the probe and switching system of FIG. 15, further providing multiple ground pads for switching between a number of possible bipolar and monopolar ablation arrangements.

Referring now to FIG. 17 another embodiment of the RF probe 101 is shown. Here a series of ground pads 50a, 50b, and 50c are selectively connected to a ground connection 114 through single pole, single throw switches 120, 122, and 124. Operation of this system is as described above with reference to FIG. 15. Here, however, the controller 56 can further select between the various ground pads 50a, 50b, and 50c to promote current flow in various directions and at various power levels. Activation and deactivation of current paths can, again, be determined by the controller 56 based on feedback from thermal sensors 30 or other types of feedback as described above. Furthermore, thermal sensors 30 can also be coupled to the ground pads 50a, 50b, and 50c, or to the ground pads shown in any of the configurations described above, and temperature readings from the sensors can be used to determine switching parameters. Similarly, impedance between a selected prong and a selected ground pad can also be used as a switching parameter. Various other ablation processes between electrodes and multiple ground pads are disclosed in co-ending provisional patent application 60/569,896, filed May 11, 2004, entitled "Radiofrequency Ablation with Independently Controllable Ground Pad Conductors" which is hereby incorporated herein by reference for its description of independently controllable ground pads and methods for controlling such devices. The methods described therein for switching between electrodes and ground pads can also be applied between individual prongs as described herein, and ground pads.

Although specific embodiments of electrodes have been shown and described here, it will be apparent that electrodes can be constructed with various numbers of electrically isolated prongs, and that various types of switching arrangements can be provided between the prongs. Furthermore, construction in which some prongs in any electrode are connected together while others are electrically isolated can also be provided. Additionally, although temperature sensor feedback is shown and described, it will be apparent that any of the feedback mechanisms described above could also be used in conjunction with electrodes having electrically isolated probes. Furthermore, although a single electrode 101 is shown and described, it will be apparent that multiple electrodes could be used in a single treatment, each of the electrodes being individuals controlled either by independent or multiple controllers. The probe itself can be an umbrella probe or, in the alternative, comprise a plurality of electrically independent needles or prongs housed together in a single shaft.

It is specifically intended that the present invention not be limited to the embodiments and illustrations contained herein, but include modified forms of those embodiments including portions of the embodiments and combinations of elements of different embodiments as come within the scope of the following claims. For example, the switch may be implemented using multiple radiofrequency sources that are enabled and disabled appropriately. Hybrid systems in which multiple electrodes are energized simultaneously and alternating are also contemplated. While percutaneous electrodes are described, the invention is also applicable to cauterizing probes and operative or laparoscopically placed electrodes.

We claim:

1. A radiofrequency ablation system comprising:
   an electric probe comprising a plurality of prongs, each of the plurality of prongs being electrically isolated from the others of the plurality of prongs, the electric probe including pairs of opposing, spaced apart prongs, the pairs being angularly spaced around a central treatment area between each pair of prongs;
   a radiofrequency power source;
   and
   a switch system communicating with the prongs and the radiofrequency power source to selectively energize the respective pairs of opposing prongs, wherein the switching system selectively connects each pair of prongs to the radiofrequency power source, the pairs of prongs being energized sequentially to provide a high temperature treatment area in the central area between the pairs of prongs.

2. The radiofrequency ablation system of claim 1 wherein the switch system changes the connected prongs and ground prongs.

3. The radiofrequency ablation system of claim 1 wherein the electronic switch controls the relative duration of the connection of the prongs to the power supply according to a control parameter selected from the group consisting of impedance between the connected prong and the ground plane, temperature of the connected prong, temperature of the ground pad, a predetermined time setting, and power dissipated between the connected prong and the ground pad.

4. The radiofrequency ablation system of claim 1 wherein the electronic switch includes a proportional/integral controller, controlling the switching according to a parameter selected from the group consisting of impedance between the connected prong and the ground plane, temperature of the connected prong, temperature of the ground pad, a predetermined time period, and power dissipated between the connected prong and the ground pad.

5. The radiofrequency ablation system of claim 1 wherein the switching system further selectively communicates with a ground connection, the switching system selectively connecting either a prong or a ground pad to the ground connection to selectively provide at least one of bipolar and monopolar ablation.

6. The radiofrequency ablation system of claim 1 further comprising a plurality of ground pads, the switch system communicating further with the ground pads and a ground connection to selectively connect at least one of the ground pads to the ground connection to provide for ablative current between the connected prong and the connected ground pad.

7. The radiofrequency ablation system of claim 6 wherein the switch system communicating with the prongs and the radiofrequency power source sequentially connects only one prong and one ground pad to the power source at a time to provide for monopolar ablative current flow from the selected prong while inhibiting current flow from the other prongs.

8. The radiofrequency ablation system of claim 1 further comprising a controller for driving the switch system.

9. The radiofrequency ablation system of claim 8 wherein the probe is an umbrella shaped electrode having at least two prongs.

10. A method of radiofrequency ablation comprising the steps of:
(a) placing an electrode including a plurality of electrically isolated prongs in contact with a patient, the electrode including pairs of opposing, space apart prongs, the pairs being angularly spaced around a central treatment area between each pair of prongs; and
(b) selectively energizing the respective pairs of opposing prongs; and
(c) energizing the pairs of opposing prongs in sequence to provide a high temperature treatment area in the central area between the pairs of prongs.

11. The method recited in claim 10 wherein the electrode probe is an umbrella electrode having at least two electrode wires extending from a common shaft.

12. The method recited in claim 10 wherein the plurality of prongs are arranged in a parallel configuration.

13. The method recited in claim 10 wherein the relative duration of the connection of the prongs of electrodes to the power supply is according to a control parameter selected from the group consisting of impedance between the connected prong and the ground connection, temperature of at least one of the connected pairs of electrodes, and power dissipated between the connected pairs of the electrodes.

14. The method recited in claim 10 wherein the connection of the power supply to one of at lease of one of the prongs is controlled by a proportional/integral controller according to a parameter selected from the group consisting of impedance between the connected prong and ground connection, temperature at least one of the connected prong and ground connection, and power dissipated between the connected prong and ground connection.

15. The method recited in claim 10 further including the step of adjusting the radiofrequency power source output according to a control parameter selected from the group consisting of impedance between the connected prong and ground connection, temperature of at least one of the connected prong and ground connection, and power dissipated between the connected prong and ground connection.

16. The method as recited in claim 10 further comprising the step of placing at least one ground pad in contact with the patient and selectively connecting the power source between one of the electrically isolated prongs and the ground pad.

17. The method as recited in claim 16 further comprising the step of selectively connecting between the plurality of probes and the ground pad to selectively provide monopolar and bipolar ablation.

* * * * *

UNITED STATES PATENT AND TRADEMARK OFFICE
CERTIFICATE OF CORRECTION

PATENT NO. : 7,520,877 B2  
APPLICATION NO. : 10/911927  
DATED : April 21, 2009  
INVENTOR(S) : Fred T. Lee, Jr. et al.

Page 1 of 1

It is certified that error appears in the above-identified patent and that said Letters Patent is hereby corrected as shown below:

IN THE CLAIMS:

CLAIM 14, column 16, line 26, delete "lease" and substitute therefor -- least --.

Signed and Sealed this
Nineteenth Day of June, 2012

David J. Kappos
*Director of the United States Patent and Trademark Office*